… … …

United States Patent [19]

Gustavson et al.

[11] Patent Number: 5,250,666

[45] Date of Patent: Oct. 5, 1993

[54] RADIONUCLIDE METAL CHELATES FOR THE RADIOLABELING OF PROTEINS

[75] Inventors: Linda M. Gustavson, Seattle; Ananthachari Srinivasan; Sudhakar Kasina, both of Kirkland; Alan R. Fritzberg, Edmonds, all of Wash.

[73] Assignee: NeoRx Corporation, Seattle, Wash.

[21] Appl. No.: 973,048

[22] Filed: Nov. 6, 1992

Related U.S. Application Data

[60] Division of Ser. No. 577,959, Sep. 5, 1990, Pat. No. 5,164,176, which is a continuation-in-part of Ser. No. 367,502, Jun. 16, 1989, abandoned.

[51] Int. Cl.⁵ ............................................... A61K 43/00
[52] U.S. Cl. .................................. 530/391.5; 424/1.1; 534/10; 534/14
[58] Field of Search ...................... 503/391.5; 424/1.1; 534/10, 14

[56] References Cited

U.S. PATENT DOCUMENTS 4,444,690  4/1984  Fritzberg et al. .
4,670,545  6/1987  Fritzberg et al. .
4,673,562  6/1987  Davison et al. .
4,849,511  7/1989  Verbruggen .
4,861,869  8/1989  Nicolotti et al. .
4,883,862 11/1989  Chervu et al. .
4,897,255  1/1990  Fritzberg et al. .
4,925,650  5/1990  Nosco et al. .
4,963,682 10/1990  Bodor et al. ..................... 424/1.1
4,963,688 10/1990  Bodor et al. ..................... 424/1.1

FOREIGN PATENT DOCUMENTS 0173424  3/1985  European Pat. Off. .
0284071  9/1988  European Pat. Off. .
0300431  1/1989  European Pat. Off. .

Primary Examiner—David L. Lacey
Assistant Examiner—F. C. Eisenschenk
Attorney, Agent, or Firm—Seed and Berry

[57] ABSTRACT

Chelating compounds of specified structure are useful for radiolabeling targeting proteins such as antibodies. The radiolabeled antibodies, or catabolites thereof, demonstrate improved biodistribution properties, including reduced localization within the intestines.

16 Claims, 7 Drawing Sheets

34

35

36

Synthesis of succinate reagent 16 via oxathiolone

Synthesis of succinate reagent 16 using LDA

34

35

36

RADIONUCLIDE METAL CHELATES FOR THE RADIOLABELING OF PROTEINS

CROSS REFERENCE TO RELATED APPLICATIONS

This application is a divisional application of U.S. Ser. No. 07/577,959, now U.S. Pat. No. 5,164,176, which is a continuation-in-part of U.S. patent application Ser. No. 07/367,502, filed Jun. 16, 1989, now abandoned.

BACKGROUND

Radiolabeled antibodies are used in a variety of diagnostic and therapeutic medical procedures. The increased specificity of monoclonal antibodies, compared to polyclonal antibodies, makes them even more useful for delivering diagnostic or therapeutic agents such as radioisotopes to desired target sites in vivo. A monoclonal antibody specific for a desired type of target cells such as tumor cells may be used to deliver a therapeutic radionuclide attached to the antibody to the target cells, thereby causing the eradication of the undesired target cells. Alternatively a monoclonal antibody having a diagnostically effective radionuclide attached thereto may be administered, whereupon the radiolabeled antibody localizes on the target tissue. Conventional diagnostic procedures then may be used to detect the presence of the target sites within the patient.

One method for radiolabeling proteins such as antibodies involves attachment of radionuclide metal chelates to the proteins. Chelates having a variety of chemical structures have been developed for this purpose. The usefulness of such chelates is dependent upon a number of factors such as the stability of radionuclide binding within the chelate and the reactivity of the chelate with the desired protein. The efficiency of radiolabeling of the chelating compound to produce the desired radionuclide metal chelate also is important. Another consideration is the biodistribution of the radiolabeled antibody and catabolites thereof in vivo. Localization in non-target tissues limits the total dosage of a therapeutic radiolabeled antibody that can be administered, thereby decreasing the therapeutic effect. In diagnostic procedures, localization in non-target tissues may cause undesirable background and/or result in misdiagnosis. The need remains for improvement in these and other characteristics of radionuclide metal chelate compounds used for radiolabeling of proteins such as antibodies.

SUMMARY OF THE INVENTION

The present invention provides a compound of the formula:

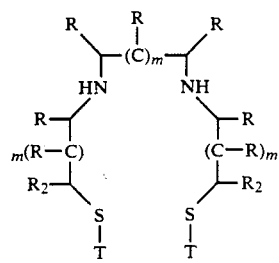

wherein:

each R independently represents $=O$, $H_2$, a lower alkyl group, $-(CH_2)_n-COOH$, or $R_1-Z$;

n is 0 to about 3;

$R_1$ represents a lower alkyl or substituted lower alkyl group;

Z represents a protein conjugation group or a targeting protein;

each $R_2$ independently represents $H_2$, a lower alkyl group, $-(CH_2)_n-COOH$, or $R_1-Z$;

each m is 0 or 1, with at most one $m=1$;

each T represents a sulfur protecting group; and the compound comprises at least one $-(CH_2)_n-COOH$ substituent and one $-R_1-Z$ substituent.

The present invention also provides radionuclide metal chelate compounds of the formula:

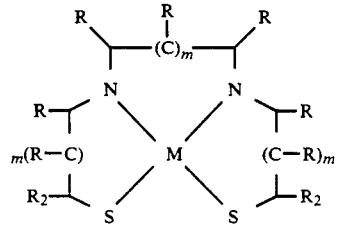

wherein:

M represents a radionuclide metal or oxide thereof and the other symbols are as described above.

These compounds comprise a targeting protein such as an antibody, or a conjugation group for attachment of the compound to a targeting protein. The chelating compound may be attached to a targeting protein and subsequently radiolabeled. Alternatively, the radionuclide metal chelate compound may be prepared and then attached to a targeting protein. The resulting radiolabeled targeting proteins are useful in diagnostic and therapeutic medical procedures. An example of a targeting protein is a monoclonal antibody that binds to cancer cells.

The carboxylic acid substituent(s) on the compounds of the present invention are believed to assist in chelation of a radionuclide and to contribute to improved biodistribution properties of catabolites of the radiolabeled targeting proteins. Reduced localization of radioactivity within the intestines is achieved using the radiolabeled targeting proteins of the present invention.

DETAILED DESCRIPTION OF THE INVENTION

Figure 1:
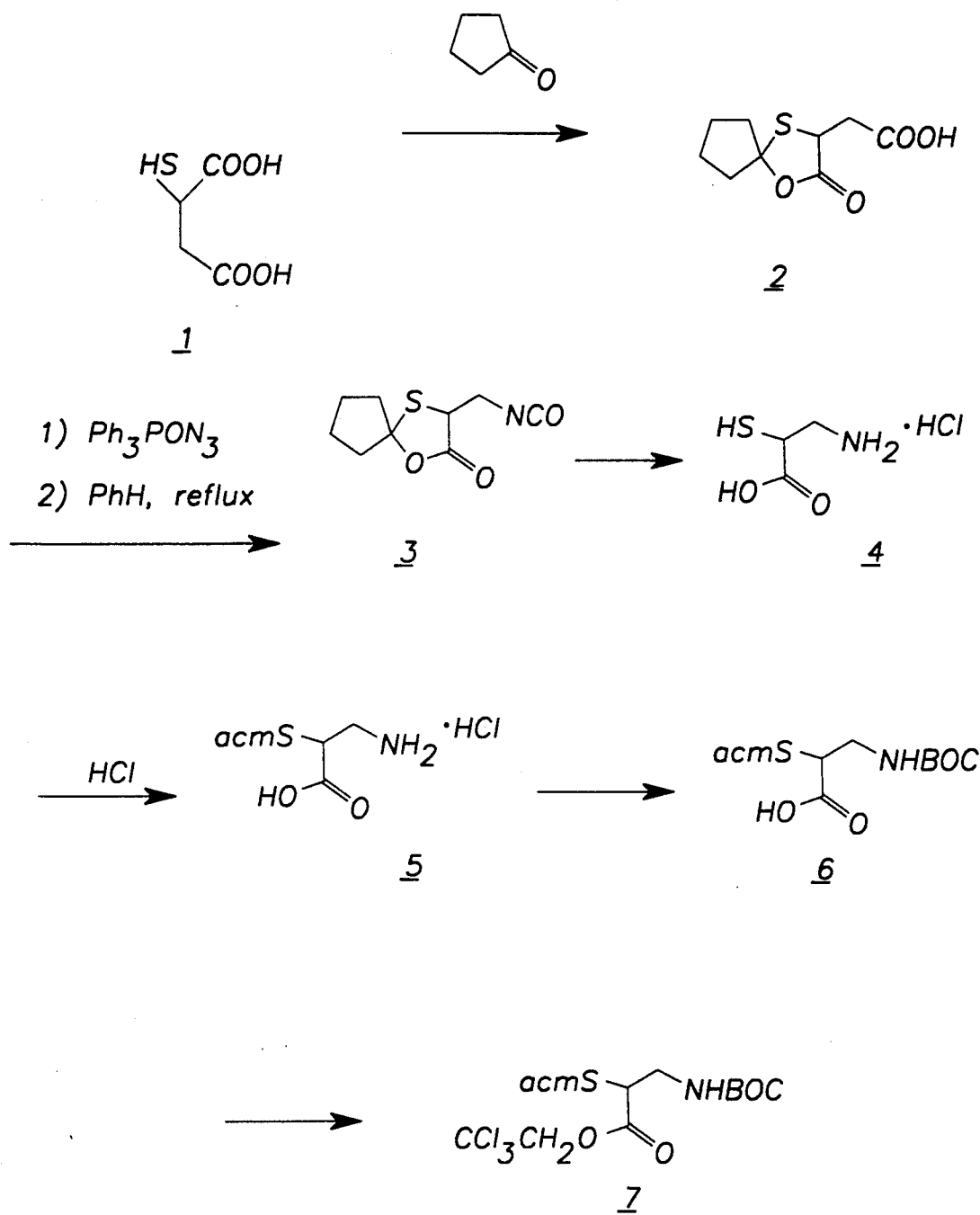
FIGS. 1-7 depict chemical synthesis procedures that may be used to prepare certain chelating compounds of the present invention.

The present invention provides chelating compounds and radionuclide metal chelate compounds prepared therefrom, as well as radiolabeled proteins having the chelates attached thereto. The radionuclide metal chelates of the present invention are attached to targeting proteins such as antibodies to form radiolabeled targeting proteins having diagnostic or therapeutic use. The compounds each comprise a targeting protein or a protein conjugation group for attachment of the compound to a targeting protein. The compounds also comprise at least one carboxylic acid substituent. The good radiolabeling yields (i.e., chelate formation) achieved with these compounds are believed to be attributable, at least in part, to the presence of the carboxylic acid substituent(s). The improved biodistribution properties of the radiolabeled proteins of the invention also are believed to be at least in part attributable to the carboxylic acid substituent(s) on the chelate.

Provided by the present invention are chelating compounds of the following formula:

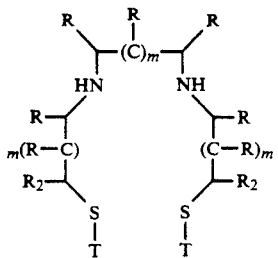

wherein:
each R independently represents =O, H$_2$, a lower alkyl group, —(CH$_2$)$_n$—COOH, or R$_1$—Z;
n is 0 to 3;
R$_1$ represents a lower alkyl or substituted lower alkyl group;
Z represents a protein conjugation group or a targeting protein;
each R$_2$ independently represents H$_2$, a lower alkyl group, —(CH$_2$)$_n$—COOH, or R$_1$—Z;
each m is 0 or 1, with at most one m=1;
each T represents a sulfur protecting group; and
the compound comprises at least one —(CH$_2$)$_n$—COOH substituent and one —R$_1$—Z substituent.

The above presented chelating compounds are radiolabeled to form the corresponding radionuclide metal chelates of the following formula:

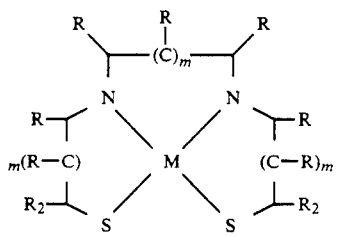

wherein:
M represents a radionuclide metal or an oxide thereof and all the other symbols are as described above.

A protein conjugation group is a chemically reactive functional group that will react with a protein under conditions that do not denature or otherwise adversely affect the protein. The protein conjugation group therefore is sufficiently reactive with a functional group on a protein so that the reaction can be conducted n substantially aqueous solutions and does not have to be forced, e.g. by heating to high temperatures, which may denature the protein. Examples of suitable protein conjugation groups include but are not limited to active esters, isothiocyanates, amines, hydrazines, thiols, and maleimides. Among the preferred active esters are thiophenyl ester, 2,3,5,6-tetrafluorophenyl ester, and 2,3,5,6-tetrafluorothiophenyl ester. The preferred active esters may comprise a group that enhances water solubility, at the para (i.e., 4) position on the phenyl ring. Examples of such groups are CO$_2$H, SO$_3^-$, PO$_3^{2-}$, OPO$_3^{2-}$, and O(CH$_2$CH$_2$O)$_n$CH$_3$ groups.

The protein conjugation group (represented as Z in the above-presented formulas) is attached to the chelating compound core through the linkage represented as R$_1$. R$_1$ is a lower alkyl or substituted lower alkyl group. By "lower alkyl" is meant an alkyl group of preferably one to four carbon atoms. Most preferably, R$_1$ is a methylene chain comprising from two to three carbon atoms. The lower alkyl group may be substituted with hetero atoms such as oxygen or nitrogen atoms. When the protein conjugation group is a primary amine, the R$_1$ linkage comprises a methylene group immediately adjacent to the terminal primary amine protein conjugation group.

The term "targeting protein" as used herein refers to proteins which are capable of binding to a desired target site in vivo. The targeting protein may bind to a receptor, substrate, antigenic determinant, or other binding site on a target cell or other target site. The targeting protein serves to deliver the radionuclide attached thereto to the desired target site in vivo. Examples of targeting proteins include, but are not limited to, antibodies and antibody fragments, hormones, fibrinolytic enzymes, and biologic response modifiers. The term "targeting protein" includes proteins, polypeptides, and fragments thereof. In addition, other molecules that localize in a desired target site in vivo, although not strictly proteins, are included within the definition of the term "targeting proteins" as used herein. For example, certain carbohydrates or glycoproteins may be used in the present invention. The proteins may be modified, e.g., to produce variants and fragments thereof, as long as the desired biological property (i.e., the ability to bind to the target site) is retained. The proteins may be modified by using various genetic engineering or protein engineering techniques.

Among the preferred targeting proteins are antibodies, most preferably monoclonal antibodies. A number of monoclonal antibodies that bind to a specific type of cell have been developed, including monoclonal antibodies specific for tumor-associated antigens in humans. Among the many such monoclonal antibodies that may be used are anti-TAC, or other interleukin-2 receptor antibodies; 9.2.27 and NR-ML-05 to the 250 kilodalton human melanoma-associated proteoglycan; and NR-LU-10 to a pancarcinoma glycoprotein. The antibody employed in the present invention may be an intact (whole) molecule, a fragment thereof, or a functional equivalent thereof. Examples of antibody fragments are F(ab')$_2$, Fab', Fab, and F$_v$ fragments, which may be produced by conventional methods or by genetic or protein engineering.

Targeting proteins are rarely completely specific for a desired target site. Localization in non-target tissues may occur through cross-reactivity or non-specific uptake, for example. In the case of radiolabeled targeting proteins, such localization at non-target sites may result in decreased clarity of diagnostic images (due to the increased "background") and misdiagnosis. Exposure of non-target tissues to radiation also occurs, which is especially undesirable in therapeutic procedures. The improved biodistribution properties of the radiolabeled targeting proteins of the present invention are believed to be attributable to the effect of the chelate, most likely on the biodistribution of catabolites of the radiolabeled proteins.

The chelating compounds of the present invention comprise two nitrogen and two sulfur donor atoms, and thus may be termed "N2S2" chelating compounds. The radiolabeled targeting proteins of the present invention exhibit certain improved biodistribution properties compared to targeting proteins radiolabeled with certain other N2S2 chelates. Most notably, localization of radiolabeled targeting proteins (or catabolites thereof) within the intestines is reduced.

Targeting proteins radiolabeled with certain N2S2 radionuclide metal chelates are described, for example, in European Patent Application Publication No. 188,256. When the radiolabeled proteins of EP No. 188,256 are administered in vivo, a percentage of the injected dosage of the radionuclide becomes localized within the intestines (i.e., becomes part of the intestinal contents, rather than binding to intestinal epithelial tissue per se). Although stable attachment of radionuclides to antibodies and effective localization thereof on target tumors has been achieved using the EP No. 188,256 system, reduction of the intestinal localization would be beneficial. A portion of the non-target-bound administered radiolabeled proteins (e.g., antibodies or fragments thereof) most likely is first metabolized to produce radiolabeled catabolites that subsequently enter the intestines, probably through hepatobiliary excretion. When the chelate is attached to lysine residues of the targeting protein, a major catabolite may be the lysine adduct of the chelate.

Intestinal localization of radioactivity may be confused with (or obstruct) target sites in the abdominal area. For therapeutic procedures, the dosage that can be safely administered is reduced when intestinal localization occurs (due to exposure of normal tissues to the radiation). The therapeutic effect on the target sites therefore also is reduced.

As illustrated in the examples below, the biodistribution patterns in vivo differ when targeting proteins (e.g., antibody fragments) are radiolabeled with a chelate of the present invention, compared to radiolabeling using certain other N2S2 chelates. The advantage of reduced intestinal localization is demonstrated for the radiolabeled targeting proteins of the present invention. While not wishing to be bound by theory, it is believed that the carboxylic acid substituent(s) on the chelate confer the advantageous biodistribution properties on catabolites of the radiolabeled protein (most likely lysine adducts of the chelate). The carboxylic acid substituent(s) on the compounds of the present invention increase the polarity, and therefore the water solubility, of the compounds. The increased water solubility is believed to promote excretion of the catabolites by the kidneys, resulting in efficient elimination of the radioactive catabolites in the urine. Other substituents that enhance polarity (e.g., sulfate groups) may be used on the chelating compounds, in addition to (or instead of) the COOH substituents.

Another advantage of the chelates of the present invention is the comparatively good radiolabeling yields. The free carboxylic acid substituent(s) are believed to assist in the chelation of the radionuclide.

During radiolabeling, bonds form between the four donor atoms and the radionuclide metal to form the corresponding radionuclide metal chelate. Any suitable conventional sulfur protecting group(s) may be attached to the sulfur donor atoms of the compounds of the present invention. The protecting groups should be removable, either prior to or during the radiolabeling reaction. The protecting groups attached to the two sulfur donor atoms may be the same or different. Alternatively, a single protecting group, e.g. a thioacetal group, may protect both sulfur donor atoms. Among the preferred sulfur protecting groups are acetamidomethyl and hemithioacetal protecting groups, which are displacable from the chelating compound during the radiolabeling reaction. Preferably, at least one sulfur protecting group is a hemithioacetal group, and at most one sulfur protecting group is an acetamidomethyl group.

An acetamidomethyl sulfur-protecting group is represented by the following formula, wherein the sulfur atom shown is a sulfur donor atom of the chelating compound:

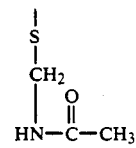

The acetamidomethyl group is displaced from the chelating compound during radiolabeling conducted at about 50° C. in a reaction mixture having a pH of about 3 to 6.

When hemithioacetal protective groups are used, each sulfur atom to be protected has a separate protective group attached to it, which together with the sulfur atom defines a hemithioacetal group. The hemithioacetal groups contain a carbon atom bonded directly (i.e., without any intervening atoms) to a sulfur atom and an oxygen atom, i.e.,

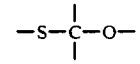

Preferred hemithioacetals generally are of the following formula, wherein the sulfur atom is a sulfur atom of the chelating compound, and a separate protecting group is attached to each of the sulfur atoms on the chelating compound:

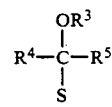

wherein R3 is a lower alkyl group, preferably of from two to five carbon atoms, and R4 is a lower alkyl group, preferably of from one to three carbon atoms. Alternatively, R3 and R4 may be taken together with the carbon atom and the oxygen atom shown in the formula to define a nonaromatic ring, preferably comprising from three to seven carbon atoms in addition to the carbon and oxygen atoms shown in the formula. R5 represents hydrogen or a lower alkyl group wherein the alkyl group preferably is of from one to three carbon atoms. Examples of such preferred hemithioacetals include, but are not limited to:

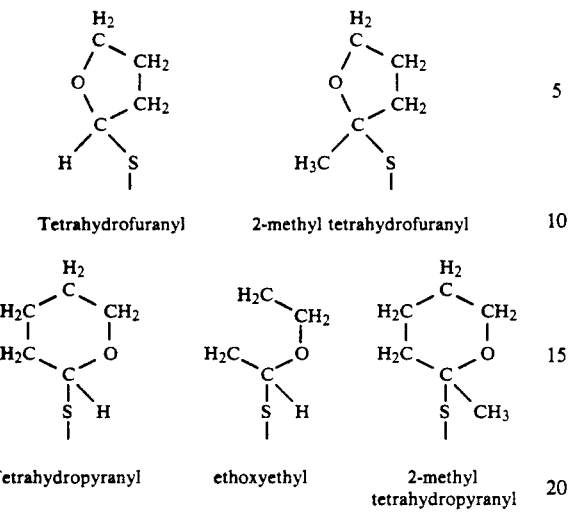

Tetrahydrofuranyl     2-methyl tetrahydrofuranyl

Tetrahydropyranyl    ethoxyethyl    2-methyl tetrahydropyranyl

These sulfur-protective groups are displaced during the radiolabeling reaction, conducted at acidic pH, in what is believed to be metal-assisted acid cleavage. Covalent bonds form between the sulfur atoms and the metal radionuclide. A separate step for removal of the sulfur-protective groups is not necessary. The radiolabeling procedure thus is simplified. In addition, the basic pH conditions and harsh conditions associated with certain known radiolabeling procedures or procedures for removal of other sulfur protective groups are avoided. Thus, base-sensitive groups on the chelating compound survive the radiolabeling step intact. Such base labile groups include any group which may be destroyed, hydrolyzed, or otherwise adversely affected by exposure to basic pH. In general, such groups include esters, maleimides, and isothiocyanates, among others. Such groups may be present on the chelating compound as protein conjugation groups.

The compounds of the present invention preferably comprise at least one =O substituent, most preferably two =O substituents. In one embodiment of the invention at least one and preferably two $R_2$ substituents are —$(CH_2)_n$—COOH, with n preferably equal to 1.

Examples of the chelating compounds of the present invention are the compounds of the following formulas:

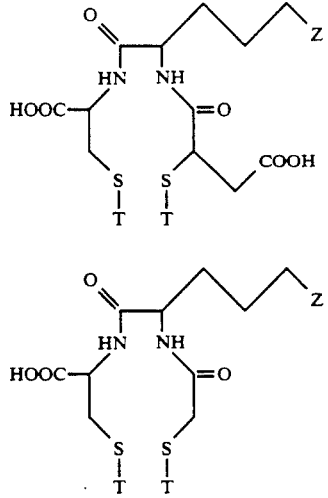

wherein the symbols are as described above. Procedures for synthesizing these compounds are presented in the examples below. In one embodiment of the invention, these chelating compounds comprise either two hemithioacetal, or one hemithioacetal and one acetamidomethyl sulfur protecting groups.

The chelating compounds of the present invention are radiolabeled, using conventional procedures, with any of a variety of radionuclide metals to form the corresponding radionuclide metal chelates. These radionuclide metals include, but are not limited to, copper (e.g., $^{67}Cu$ and $^{64}Cu$); technetium (e.g., $^{99m}Tc$); rhenium (e.g., $^{186}Re$ and $^{188}Re$); lead (e.g., $^{212}Pb$); bismuth (e.g., $^{212}Bi$); and palladium (e.g., $^{109}Pd$). Methods for preparing these isotopes are known. Molybdenum/technetium generators for producing $^{99m}Tc$ are commercially available. Procedures for producing $^{186}Re$ include the procedures described by Deutsch et al., (*Nucl. Med. Biol.* Vol. 13:4:465–477, 1986) and Vanderheyden et al. (*Inorganic Chemistry*, Vol. 24:1666–1673, 1985), and methods for production of $^{188}Re$ have been described by Blachot et al. (*Intl. J. of Applied Radiation and Isotopes* Vol. 20:467–470, 1969) and by Klofutar et al. (*J. of Radioanalytical Chem.*, Vol. 5:3–10, 1970). Production of $^{109}Pd$ is described in Fawwaz et al., *J. Nucl. Med.* (1984), 25:796. Production of $^{212}Pb$ and $^{212}Bi$ is described in Gansow et al., *Amer. Chem. Soc. Symp. Ser.* (1984), 241:215–217, and Kozah et al., *Proc. Nat'l. Acad. Sci. USA* (January 1986) 83:474–478. $^{99m}Tc$ is preferred for diagnostic use, and the other radionuclides listed above have therapeutic, use.

In one embodiment of the present invention, chelating compounds of the invention comprising acetamidomethyl and/or hemithioacetal sulfur protective groups are radiolabeled with a metal radionuclide by reacting the compound with the radionuclide under conditions of acidic pH. It is believed that the acidic pH and the presence of the metal both contribute to the displacement of the sulfur protective groups from the chelating compound. The radionuclide is in chelatable form when reacted with the chelating compounds of the invention.

In the case of technetium and rhenium, being in "chelatable form" generally requires a reducing step. a reducing agent will be employed to reduce the radionuclides (e.g., in the form of pertechnetate and perrhenate, respectively) to a lower oxidation state at which chelation will occur. Many suitable reducing agents, and the use thereof, are known. (See, for example, U.S. Pat. Nos. 4,440,738; 4,434,151; and 4,652,440.) Such reducing agents include, but are not limited to, stannous ion (e.g., in the form of stannous salts such as stannous chloride or stannous fluoride), metallic tin, ferrous ion (e.g., in the form of ferrous salts such as ferrous chloride, ferrous sulfate, or ferrous ascorbate) and many others. Sodium pertechnetate (i.e., $^{99m}TcO_4-$ which is in the +7 oxidation level) or sodium perrhenate (i.e., $^{188}ReO_4-$, $^{186}ReO_4-$) may be combined simultaneously with a reducing agent and a chelating compound of the invention in accordance with the radiolabeling method of the invention, to form a chelate.

Preferably, the radionuclide is treated with a reducing agent and a complexing agent to form an intermediate complex (i.e., an "exchange complex"). Complexing agents are compounds which bind the radionuclide more weakly than do the chelate compounds of the invention, and may be weak chelators. Any of the suitable known complexing agents may be used, including but not limited to gluconic acid, glucoheptonic acid, methylene disphosphonate, glyceric acid, glycolic acid, mannitol, oxalic acid, malonic acid, succinic acid, bicine, N,N'-bis(2-hydroxy ethyl) ethylene diamine, citric acid, ascorbic acid and gentisic acid. Good results are obtained using gluconic acid or glucoheptonic acid as the Tc-complexing agent and citric acid for rhenium. When the radionuclide in the form of such an exchange complex is reacted with the chelating compounds of the invention, the radionuclide will transfer to these compounds which bind the radionuclide more strongly to form chelates of the invention. Heating is often required to promote transfer of the radionuclide. Radionuclides in the form of such complexes also are considered to be in "chelatable form" for the purposes of the present invention.

Chelates of $^{212}Pb$, $^{212}Bi$, and $^{109}Pd$ may be prepared by combining the appropriate salt of the radionuclide with the chelating compound and incubating the reaction mixture at room temperature or at higher temperatures. It is not necessary to treat the lead, bismuth, palladium, and copper radioisotopes with a reducing agent prior to chelation, as such isotopes are already in an oxidation state suitable for chelation (i.e., in chelatable form). The specific radiolabeling reaction conditions may vary somewhat according to the particular radionuclide and chelating compound involved.

The chelating compound may be radiolabeled to form a radionuclide metal chelate, which then is reacted with a targeting protein. Alternatively, the unlabeled chelating compound may be attached to the targeting protein and subsequently radiolabeled. Proteins contain a variety of functional groups; e.g., carboxylic acid (COOH) or free amine (—NH$_2$) groups, which are available for reaction with a suitable protein conjugation group "Z" on a chelator to bind the chelator tc the protein. For example, an active ester on the chelator reacts with primary amine groups on lysine residues of proteins to form amide bonds. Alternatively, the protein and/or chelator may be derivatized to expose or attach additional reactive functional groups. The derivatization may involve attachment of any of a number of linker molecules such as those available from Pierce Chemical Company, Rockford, Ill. (See the Pierce 1986-87 General Catalog, pages 313-54.) Alternatively, the derivatization may involve chemical treatment of the protein (which may be an antibody). Procedures for generation of free sulfhydryl groups on antibodies or antibody fragments are also known. (See U.S. Pat. No. 4,659,839.) Maleimide conjugation groups on a chelator are reactive with the sulfhydryl (thiol) groups.

Alternatively, when the targeting compound is a carbohydrate or glycoprotein, derivatization may involve chemical treatment of the carbohydrate; e.g., glycol cleavage of the sugar moiety of a glycoprotein antibody with periodate to generate free aldehyde groups. The free aldehyde groups on the antibody may be reacted with free amine or hydrazine conjugation groups on the chelator to bind the chelator thereto. (See U.S. Pat. No. 4,671,958.)

The radiolabeled targeting proteins of the present invention have use in diagnostic and therapeutic procedures, both for in vitro assays and for in vivo medical procedures. The radiolabeled proteins may be administered intravenously, intraperitoneally, intralymphatically, locally, or by other suitable means, depending on such factors as the type of target site. The amount to be administered will vary according to such factors as the type of radionuclide (e.g., whether it is a diagnostic or therapeutic radionuclide), the route of administration, the type of target site(s), the affinity of the targeting protein for the target site of interest, and any cross-reactivity of the targeting protein with normal tissues. Appropriate dosages may be established by conventional procedures and a physician skilled in the field to which this invention pertains will be able to determine a suitable dosage for a patient. A diagnostically effective dose is generally from about 5 to about 35 and typically from about 10 to about 30 mCi per 70 kg body weight. A therapeutically effective dose is generally from about 20 mCi to about 300 mCi. For diagnosis, conventional non-invasive procedures (e.g., gamma cameras) are used to detect the biodistribution of the diagnostic radionuclide, thereby determining the presence or absence of the target sites of interest (e.g., tumors).

The comparatively low intestinal localization of the therapeutic radiolabeled antibodies of the present invention or catabolites thereof permits increased dosages, since intestinal tissues are exposed to less radiation. The clarity and accuracy of diagnostic images also is improved by the reduced localization of radiolabeled antibodies or catabolites thereof in normal tissues.

The following examples are presented to illustrate certain embodiments of the present invention.

EXAMPLE I

Synthesis of S-acetamidomethyl-N-t-BOC Isocysteine Trichloroethyl Ester

The synthesis procedure is outlined in FIG. 1.

Preparation of S-acetamidomethyl-N-t-BOC isocysteine 6 from 1

Mercaptosuccinic acid 1 (commercially available) was reacted with cyclopentanone in TosOH to form 2-oxathiolone To a solution of 2-oxathiolone 2 in benzene (40 mL) and triethylamine (3.28 mL, 23.55 mmol) at 0° C., was added a solution of diphenyl phosphorylazide (5.08 mL, 23.55 mmol) in benzene (5.0 mL). The ice bath was removed and the reaction solution was stirred at room temperature for 1 hour. The solution was washed with water. The water was extracted with benzene. The combined benzene extracts were dried, concentrated to half the original volume, and heated under reflux in an oil bath gradually raised in temperature from 50° C. to 80° C. over 1 hour. The reaction solution was cooled to room temperature, diluted with ethyl acetate (50 mL) and washed twice with a saturated solution of NaHCO$_3$ (30 mL.) The organic extracts were dried (MgSO$_4$) and evaporated to give the crude isocyanate 3 as a brown oil (4.92 g).

A suspension of 3 in 6N HCl (45 mL) was heated under reflux for 40 minutes. The reaction solution was cooled, washed twice with ethyl acetate (50 mL). Evaporation of the aqueous extract gave crude isocysteine 4 as an amber oil (4.92 g, theoretical 3.64 g). NMR shows isocysteine plus an aliphatic contaminant.

To half of the crude isocysteine 4 (2.42 g, theoretical 11.61 mmol) in water (3.0 mL) at 0° C. was added N-hydroxyacetamide (1.14 g). To this solution was added dropwise concentrated HCl (0.45 mL). The solution was stored at 0° C. for 3 days. The solution was evaporated to give S-acm isocysteine 5 as a colorless liquid NMR (D$_2$O): 1.95 (s, 3H), 3.35 (dd, 2H), 3.8 (t, 1H), 4.4 (dd, 2H). TLC (c-18, 15% meOH/H$_2$O 1% HOAc, one spot 0.4 Rf.

To a solution of 5 (theoretical 11.61 mmol) in DMF/H$_2$O 3:2, 25 mL) and triethylamine (3.60 mL, 25.54 mmol) was added di-t-butyl dicarbonate (3.04 g, 13.9 mmol). The reaction was stirred at room temperature for 3 hours and then evaporated. The residue was partitioned between water and ethyl acetate. The water layer was acidified to pH 3.0 with 1.0M HCl and further extracted with ethyl acetate (3×30 mL) and methylene chloride (2×50 mL). The combined organic extracts were dried (MgSO$_4$) and evaporated to give an oil. Purification by chromatography (15% isopropanol/methylene chloride 2% acetic acid) afforded 6 as an oil which crystallized from acetonitrile. Yield from 2- oxathiolone 2 was 1.90 g (6.21 mmol)=53%.

Conversion of S-acm N-t-BOC isocysteine 6 to S-acm N-t-BOC isocysteine trichloroethyl ester 7

To an ice cold solution of 6 (1.90 g, 6.21 mmol) and trichloroethanol (0.71 mL, 7.45 mmol) in acetonitrile (12 mL) and methylene chloride (2 mL) was added dicyclohexylcarbodiimide (DCC) (1.47 g, 7.14 mmol) and dimethylamino pyridine (76 mg, 0.62 mmol). The ice bath was allowed to melt and the reaction solution was stirred for 16 hours at room temperature. The reaction was cooled to 0° C., filtered, and evaporated to give an oil which was purified by chromatography (1:1 EtOAc/Hexanes 1% HOAc) to give 7 as an oil (1.25 g, 2.95 mmol) in 47% yield.

EXAMPLE II

Synthesis of N-t-BOC Aminoadipic Acid δ-t-butyl Ester α-succinimidyl Ester 12

Figure 2:
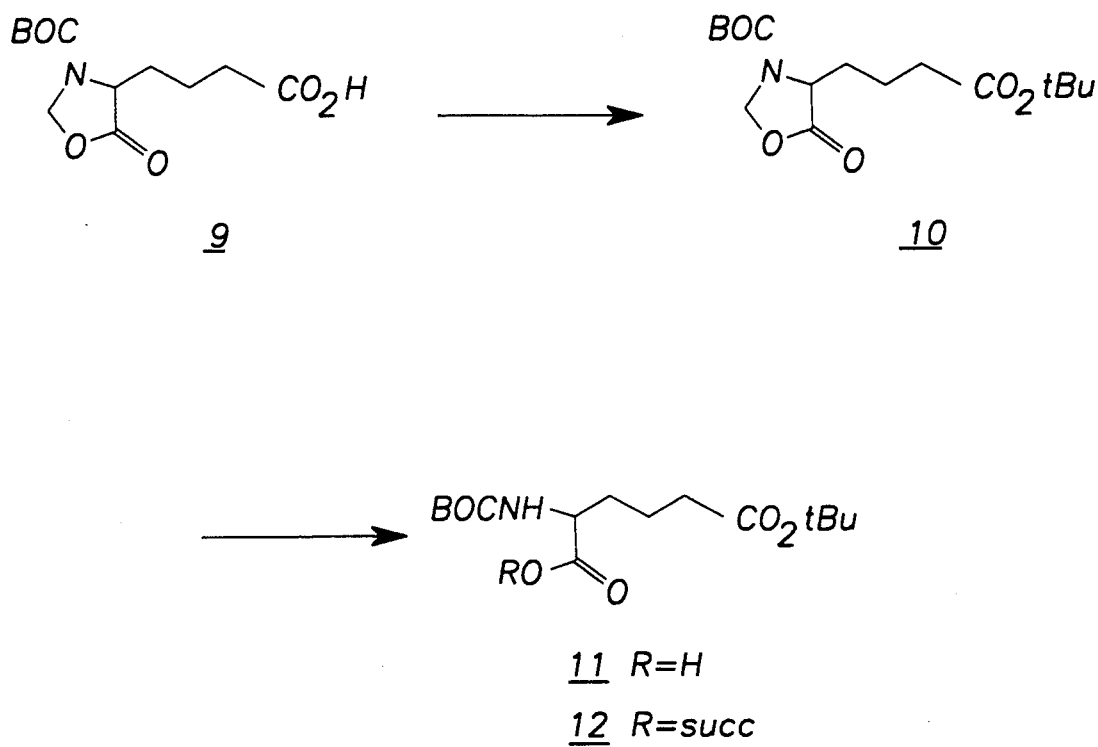

The synthesis procedure is outlined in FIG. 2.

Conversion of N-t-BOC oxazolidine aminoadipic acid (9) to N-t-BOC oxazolidine aminoadipic acid t-butyl ester (10)

To an ice cold solution of 9 (3.23 g, 12.4 mmol) in acetonitrile (12 mL) and t-butanol (1.75 mL, 18.6 mmol) were added dimethylaminopyridine (151 mg, 1.24 mmol) and DCC (3.07 g, 14.9 mmol). The reaction was stirred at 0° C. for 69 minutes and then stored at 0° C. for 60 hours. The mixture was filtered. The filtrate was evaporated to give a solid which was chromatographed (25% EtOAc/Hexanes). The t-butyl ester 10 was obtained as a white solid (2.85 g, 8.66 mmol) in 70% yield.

Conversion of 10 to N-t-BOC aminoadipic acid δ-t-butyl ester (11)

To a solution of 10 (100 mg, 0.30 mmol) in methanol (2.0 mL) was added 1N NaOH (0.33 mL) dropwise. The solution was stirred for 1 hour and then treated with ethanolamine (0.02 mL, 0.33 mmol). To this solution was added 1N NaOH (0.32 mL, 0.32 mmol). The reaction solution was stirred for 48 hours, concentrated, and then neutralized by the addition of 1N HCl (0.33 mL). The aqueous phase was extracted with EtOAc (25 mL). The aqueous phase was acidified with 1.0N HCl to pH 1 and further extracted with EtOAc (2×50 mL). The combined EtOAc extracts were dried (MgSO$_4$), and evaporated to give an oil. Chromatography (40% EtOAc/Hexanes 1% HOAc) gave 11 as a colorless oil (60 mg, 0.19 mmol) in 63% yield.

Conversion of 11 to N-t-BOC aminoadipic acid δ-t-butyl ester α-succinimidyl ester 12

To an ice cold solution of 11 (0.97 g, 3.06 mmol) in acetonitrile (6.0 mL) was added N-hydroxysuccinimide (422 mg, 3.67 mmol) and DCC (747 mg, 3.67 mmol). The ice bath was allowed to melt and the reaction solution was stirred at room temperature for 5 hours. The mixture was cooled to 0° C., treated with a few drops acetic acid, and filtered. Evaporation of the filtrate provided 12 as a white solid (1.19 g, 3.06 mmol) in 100% yield.

EXAMPLE III

Synthesis of Succinate Reagent 16

Figure 3:
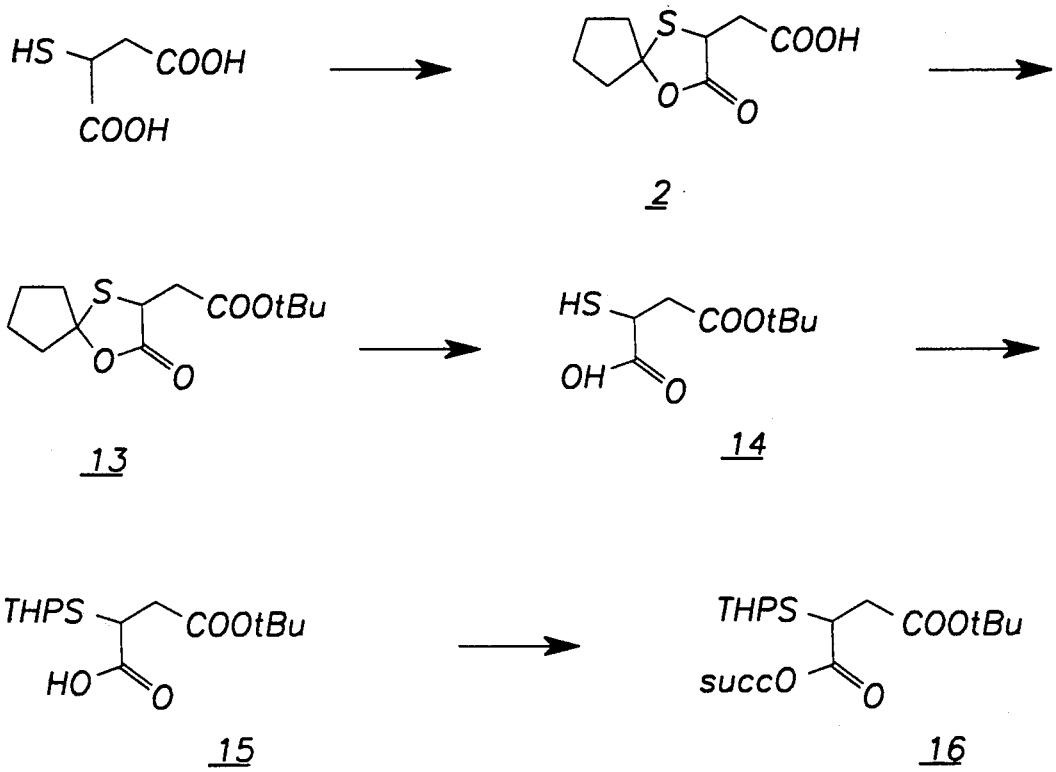
Figure 3:
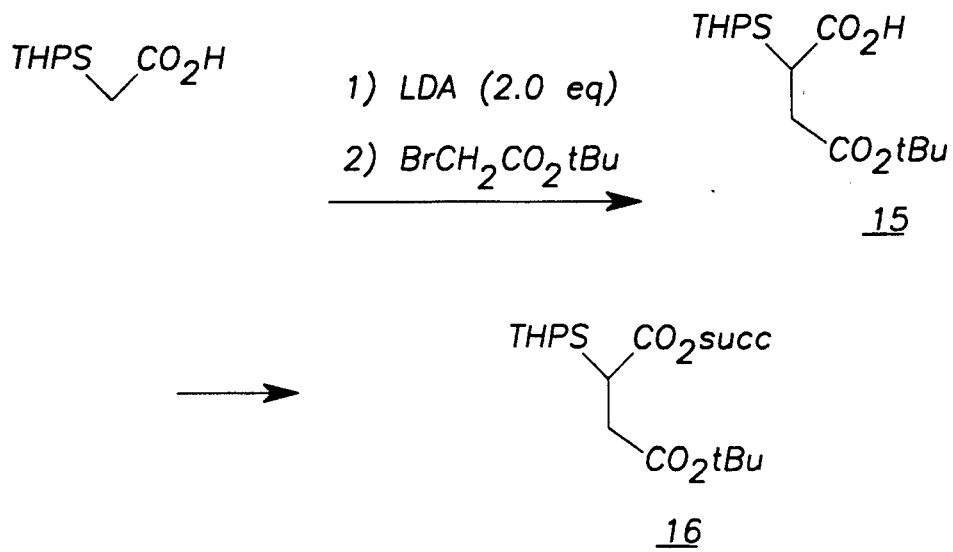

Two procedures for synthesizing compound 16 are outlined in FIG. 3.

Procedure #1: Synthesis of Succinate Reagent 16 Via Base Opening of Oxathiolone

Conversion of 2 to 2-mercaptosuccinic acid oxathiolone β-t-butyl ester 13

Compound 2 was prepared from 1 as described in Example I.

To an ice cold solution of 2 (1.45 g, 6.30 mmol) in acetonitrile (6.5 mL) and t-butanol (0.89 mL) were added dimethyl aminopyridine (77 mg, 0.63 mmol) and DCC 1.55 g, 7.56 mmol). The reaction was stirred for 1 hour at 0° C. and then stored at 0° C. for 4 days. The product was filtered. The filtrate was evaporated. Chromatography (10% EtOAc/Hexanes) provided 13 as a yellow oil (1.76 g, 6.15 mmol) in 98% yield.

Conversion of 13 to 2-mercaptosuccinic acid β-t-butyl ester (14)

To a solution of 13 (0.58 g, 1.82 mmol) in acetone (2.0 mL) was added 1N NaOH (1.82 mL, 1.82 mmol). After the reaction solution was stirred for 4 hours, additional 1N NaOH (1.82 mL, 1.82 mmol) was added. The reaction solution was stirred for 20 hours, and then neutralized by the addition of 1.0M HCl (3.6 mL). The aqueous phase was extracted with EtOAc (3×25 mL). The combined EtOAc extracts were washed with brine, dried and evaporated to give an oil. The product was chromatographed (first 10% EtOAc/Hexanes 1% HOAc, 300 mL, then 33% EtOAc/Hexanes 1% HOAc, 300 mL) to give 14 as colorless oil (0.24 g, 1.16 mmol) in 64% yield.

Conversion of 14 to S-tetrahydropyranylmercaptosuccinic acid β-t-butyl ester (15) and NHS ester 16

To a solution of 14 (240 mg, 1.16 mmol) and tosic acid monohydrate (7 mg, 0.03 mmol) in methylene chloride at −40° C. was added dihydro-2H-pyran (0.11 mL, 1.16 mmol). After the addition, the reaction was warmed to −5° C. and stirred for 30 minutes. The solvent was evaporated. The residue was dissolved in EtOAc (30 mL) and washed with pH 4.0 buffer. The aqueous phase was extracted with EtOac (2×20 mL). The combined EtOAc extracts were washed with brine, dried and evaporated to give an oil which was used without purification. The oil was dissolved in acetonitrile (2.0 mL), cooled to 0° C., and treated with N-hydroxysuccinimide (160 mg, 1.39 mmol) and DCC (287 mg, 1.39 mmol). The ice bath was allowed to melt and the reaction mixture was stirred at room temperature for 20 hours. The mixture was filtered. The filtrate was evaporated. Chromatography provided 16 as a white solid (145 mg, 0.37 mmol) in 32% yield.

Procedure #2 Synthesis of Succinate Reagent 16 Using LDA

Conversion of S-tetrahydropyranylmercaptcacetic acid (17) to S-tetrahydropyranylmercaptosuccinic acid β-t-butyl ester 15 and NHS ester 16

A solution of lithium diisopropylamide (LDA) was prepared by adding a 1.30M solution of n-butyl lithium in hexanes (13.2 mL, 17.2 mmol) to a solution of diisopropyl amine (2.52 mL, 18.0 mmol) in THF (10.0 mL) at −78° C. The solution was stirred for 20 minutes. To this was added dropwise a solution of S-tetrahydropyranyl-mercaptoacetic acid (1.32 g, 7.50 mmol) in THF (5.0 mL). The reaction became cloudy. It was stirred at −78° C. for 25 minutes, warmed to 0° C., and stirred for 25 minutes. The reaction was then cooled to −78° C. and treated with a solution of t-butyl bromoacetate (3.2 mL) in THF (2.0 mL). The reaction solution was stirred for 1 hour at −78° C., and for 30 minutes at 0° C. The reaction was quenched by the addition of acetic acid (1.0 mL) in methylene chloride. The mixture was concentrated, diluted with water and ethyl acetate. The aqueous layer was separated, acidified with 1.0M HCl to pH 3.0, and further extracted with EtOAc (2×75 mL). The combined EtOAc extracts were washed with brine, dried, and evaporated to give 15 as a canary yellow oil.

The oil was dissolved in acetonitrile (10.0 mL) and methylene chloride (1.5 mL), cooled to 0° C., and treated with N-hydroxysuccinimide (1.03 g, 9.0 mmol) and DCC (1.86 g, 9.0 mmol). The ice bath was allowed to melt and the reaction mixture was stirred for 4 hours. The mixture was cooled to 0° C. and filtered. The filtrate was evaporated to give an oil which was chromatographed (30% EtOAc/Hexanes) to give 16 as a white foam (1.36 g, 3.51 mmol) in 47% yield.

EXAMPLE IV

Synthesis of Isocys-aminoadipic-mercaptosuccinate Chelating Compound 21

Figure 4:
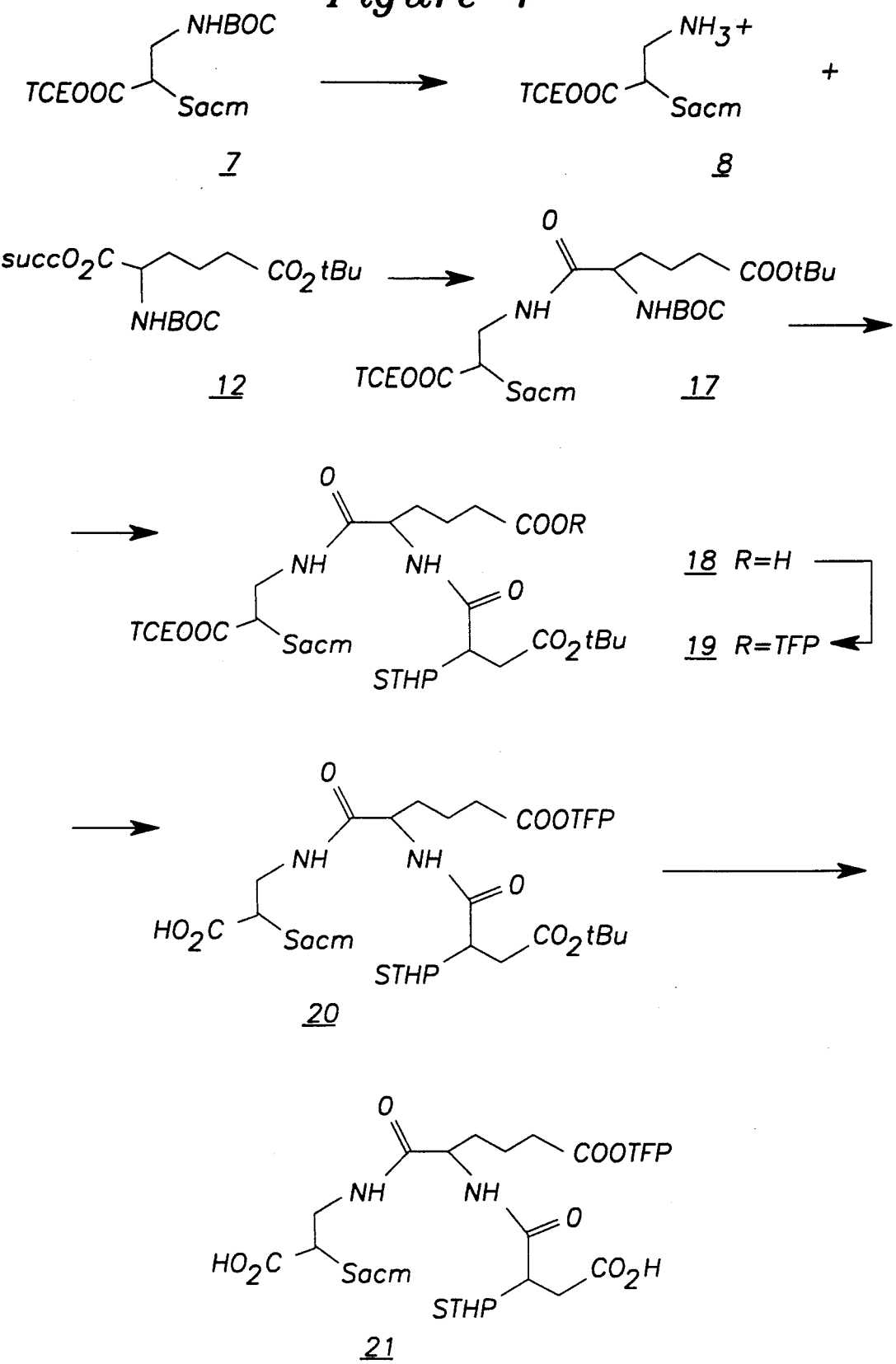

The synthesis procedure is outlined in FIG. 4.

Condensation of Cysteine 8 with Aminoadipic Acid Derivative 12 to Give 17

To an ice cold solution of S-acm N-t-BOC isocysteine trichloroethyl ester 7, prepared in Example I, (1008 mg, 2.38 mmol) in methylene chloride (7.0 mL) was added trifluoroacetic acid (6.0 mL) dropwise. The solution was stirred at room temperature for 1 hour. The solution was evaporated from carbon tetrachloride (3×50 mL). The residue was dried in vacuo for 18 hours. To an ice cold solution of the residue 8 in DMF (2.5 mL) was added a solution of 12, prepared in Example II, (867 mg, 2.22 mmol) in DMF (3.5 mL). To this was added triethylamine (0.73 mL, 5.24 mmol). The reaction was stirred at room temperature for 6 hours and then evaporated. The residue was partitioned between water and EtOAc. The aqueous phase was extracted with EtOAc (2×50 mL). The combined EtOAC extracts were washed with brine, dried, and evaporated. The product was chromatographed (50% EtOAc/Hexanes 1% HOAc) to give 17 as a white foam (1005 mg, 1.61 mmol) in 68% yield.

Condensation of 17 with Succinate Reagent 16 to Give Tripeptide 18

To an ice cold solution 17 (500 mg, 0.81 mmol) in methylene chloride (4.3 mL) was added trifluoroacetic acid (4.3 mL). The ice bath was removed and the reaction was stirred for 1 hour. The solution was evaporated from carbon tetrachloride (3×30 mL). The residue was dissolved in DMF (1.0 mL) and cooled to 0° C. To this was added a solution of 16, prepared in Example III, (376 mg, 0.97 mmol) in DMF (2 mL). Lastly triethylamine was added (0.22 mL, 1.62 mmol). The ice was allowed to melt. The reaction was stirred at room temperature for 21 hours. The solvent was evaporated. The residue was dissolved in EtOAc and washed with pH 4.0 buffer. The aqueous phase was extracted with EtOAc, then acidified with 1.0M HCl to pH 3.0, further extracted with EtOac (2×30 mL). The combined EtOAc extracts were washed with brine, dried, and evaporated. The residue was chromatographed (99:1 EtOAc:HOAc). The product 18 was obtained as a white solid in 80% yield (480 mg, 0.65 mmol).

Conversion of 18 to TFP ester 19

To an ice cold solution of 18 (480 mg, 0.65 mmol) in acetonitrile (1.5 mL) and methylene chloride (0.5 mL) were added tetrafluorophenol (140 mg, 0.84 mmol) and DCC (161 mg, 0.78 mmol). The ice bath was allowed to melt and the reaction was stirred at room temperature for 20 hours. The reaction was cooled to 0° C., treated with 2 drops acetic acid, and filtered. The filtrate was evaporated. The residue was chromatographed to give 19 as an oil (240 mg, 0.27 mmol) in 42% yield.

Cleavage of TCE ester 19 to give 20

To a solution of 19 (190 mg, 0.21 mmol) in THF (1.4 mL) and 1.0M KH$_2$PO$_4$ (0.28 mL) was added Zn dust (137 mg, 2.10 mmol). The mixture was stirred for 30 minutes. Additional phosphate buffer (0.28 mL) and Zn dust (137 mg, 2.10 mmol) were added. The reaction was stirred for 80 minutes. Additional phosphate buffer (0.25 mL), THF (1.0 mL), and Zn dust (137 mg, 2.10 mmol) were added. The reaction was filtered. The filtrate was evaporated. The residue was chromatographed to give in the first fractions recovered 19 (60 mg, 0.07 mmol), then in the later fractions 20 as a white foam (40 mg, 0.05 mmol) in 25% yield.

Cleavage of t-butyl ester 20 to give 21

A solution of 20 (40 mg, 0.05 mmol) in formic acid (1.5 mL) was stirred for 5 hours. The solution was evaporated. The product was purified by preparative LC on reverse phase semi-prep C-18 column with 45% $CH_3CN/H_2O$ 1% HOAc as mobile phase. The product 21 was obtained as a film (6 mg, 0.01 mmol) in 16% yield. The compound 21 is a chelating compound of the present invention.

EXAMPLE V

Synthesis of Cysteine Monocarboxylate Chelating Compound 28

Figure 5:
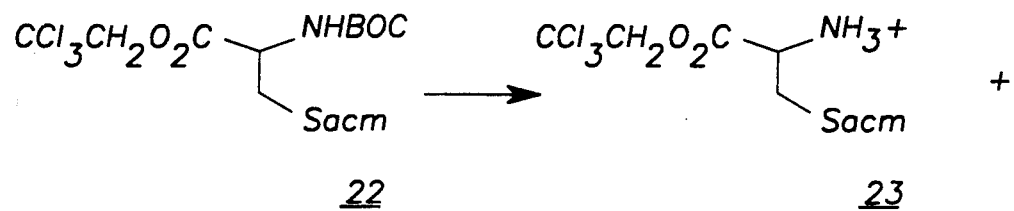
Figure 5:
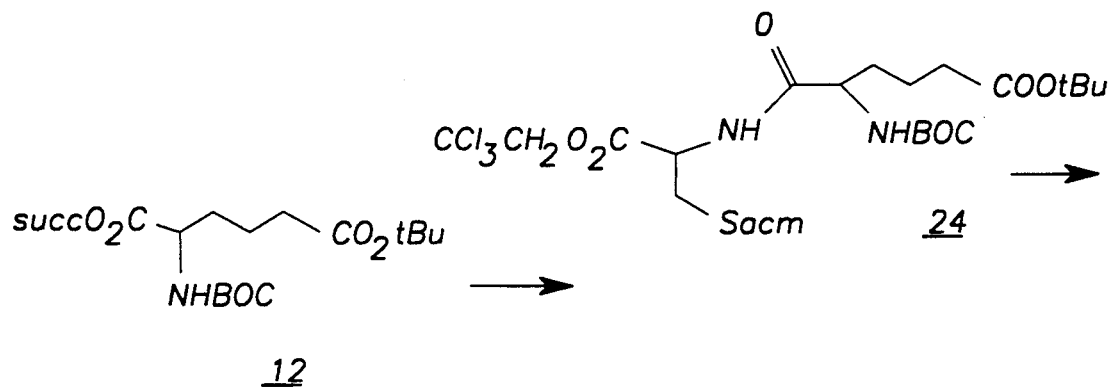
Figure 5:
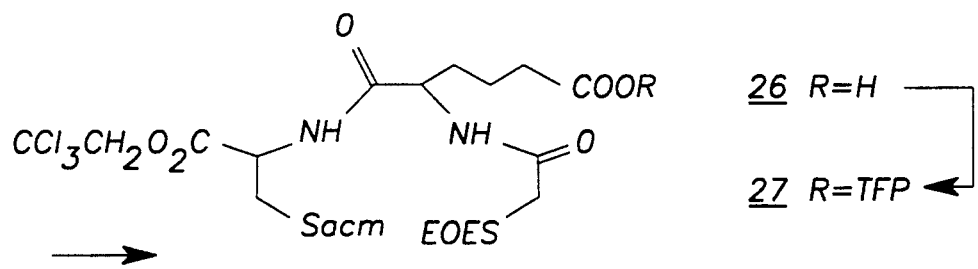
Figure 5:
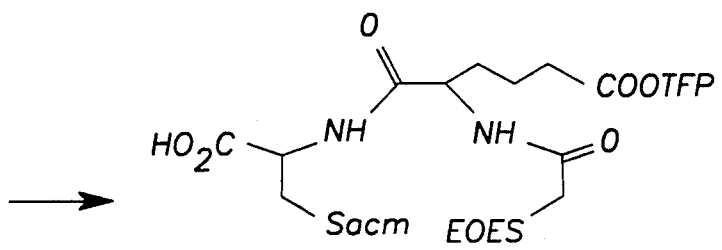

The synthesis procedure is outlined in FIG. 5.

T-BOC Cleavage and Condensation of Cysteine 22 with Aminoadipic Acid Derivative 12

To an ice cold solution of 22 (0.97 g, 2.30 mmol) in methylene chloride (6.0 mL) was added trifluoroacetic acid (6.0 mL). The reaction was stirred at room temperature, then coevaporated with carbon tetrachloride (3×15 mL) and dried in vacuo. The residue (23) was dissolved in dimethyl formamide (1.0 mL) and triethylamine (0.35 mL, 2.53 mmol). To this was added a suspension of N-t-BOC aminoadipic acidα-NHS-δ-t-butyl ester 12, prepared in Example II, (897 mg, 2.30 mmol) in DMF (2.5 mL). Triethylamine (0.35 mL, 2.53 mmol) was added and the reaction was stirred for 18 hours. The solution was concentrated. The residue was dissolved in EtOAc and washed with pH 4.0 buffer. The aqueous phase was further extracted with EtOAc (2×30 mL). The combined EtOAc extracts were washed with brine, dried, and evaporated to give an oil. Chromatography (75% EtOAc/Hexanes 1% HOAc) gave 24 as a white solid (1.40 g, 2.30 mmol) in 100% yield. FAB MS parent ions 622 and 624.

Deprotection of 24 and Condensation with S-ethoxyethyl Mercaptoacetic Acid NHS Ester to Give 26

To an ice cold solution of 24 (690 mg, 1.12 mmol) in methylene chloride (6.0 mL) was added trifluoroacetic acid (6.0 mL). The ice bath was removed and the reaction was stirred at room temperature for 2 hours. The solution was coevaporated with carbon tetrachloride (3×10 mL). The residue was dissolved in DMF and triethylamine (0.15 mL, 1.12 mmol). To this solution at 0° C. was added a solution of S-ethoxyethyl mercaptoacetic acid NHS ester (322 mg, 1.23 mmol) in DMF 2.0 mL). Lastly triethylamine (0.31 nL, 2.24 mmol) was added. The ice bath was allowed to melt and the reaction was stirred at room temperature for 18 hours. The solvent was evaporated. The residue was dissolved in EtOAc (30 mL) and washed with pH 4.0 buffer. The aqueous phase was extracted with EtOAc (2×25 mL). The combined EtOAc extracts were dried and evaporated. The residue was chromatographed (50% EtOAc/Hexanes 1% HOAc). The product 26 was obtained as an oil (380 mg, 0.55 mmol) in 50% yield.

Conversion of 26 to TFP ester 27

To a solution of 26 (190 mg, 0.31 mmol) in THF (1.8 mL) was added tetrafluorophenol (65 mg, 0.35 mmol) and DCC (73 mg, 0.35 mmol). The reaction was stirred for 20 hours, cooled to 0° C., and filtered. The filtrate was evaporated. The residue was chromatographed (99:1 EtOAc:HOAc). The product 27 was obtained as colorless oil (150 mg, 0.20 mmol) in 64% yield.

TCE ester cleavage of 27 to give cysteine ligand 28

To a solution of 27 (90 mg, 0.12 mmol in THF (0.8 mL) and 1.0M $KH_2PO_4$ buffer (0.16 mL) was added Zn dust (78 mg, 1.20 mmol). The suspension was stirred for 40 minutes. Additional phosphate buffer (0.16 mL) and Zn dust (78 mg, 1.20 mmol) were added. The reaction was stirred for 40 minutes, filtered, and rinsed with 50% aqueous acetonitrile (30 mL). The filtrate was evaporated. The residue was chromatographed (15% isopropanol/methylene chloride 2% HOAc). The product 28 was obtained as an oil (60 mg, 0.10 mmol) in 80% yield. Compound 28 is a chelating compound of the present invention.

EXAMPLE VI

Synthesis of Cysteine Succinate Chelating Compound 32

Figure 6:
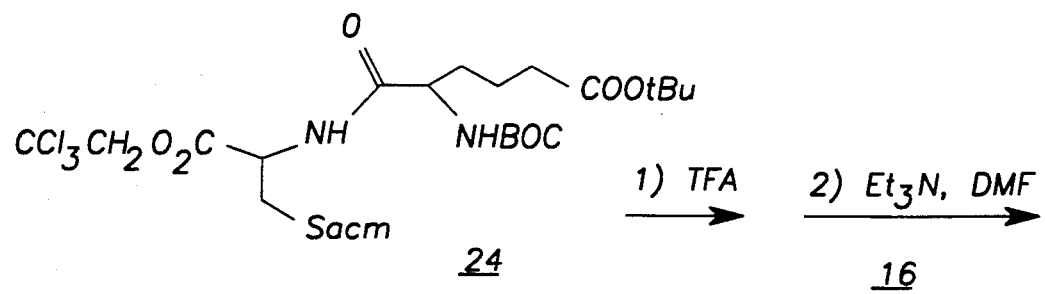
Figure 6:
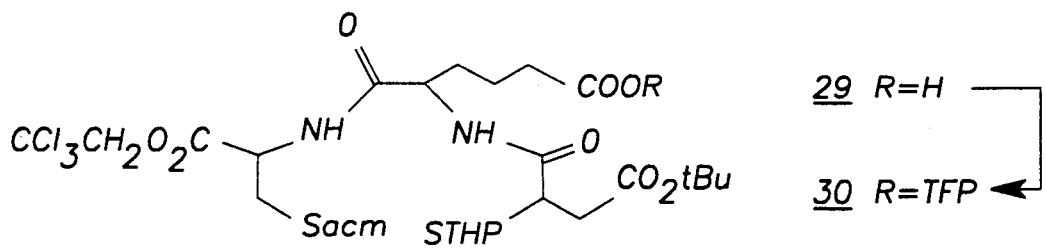
Figure 6:
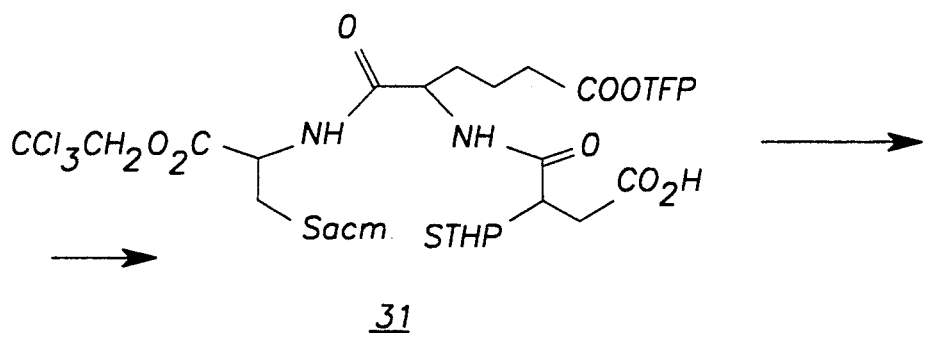
Figure 6:
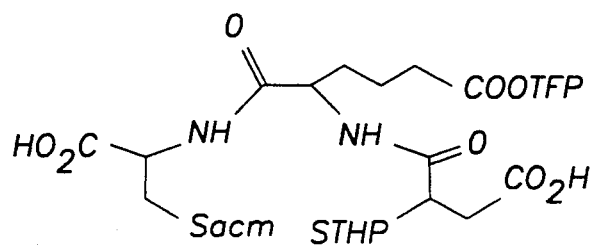

The synthesis procedure is outlined in FIG. 6.

T-BOC and T-butyl Cleavage of 24 and Condensation with Succinate Reagent 16 to Give Protected Tripeptide 29

To an ice cold solution of 24, prepared as in Example V, (708 mg, 1.16 mmol) in methylene chloride (6.2 mL) was added trifluoroacetic acid (6.2 mL). The solution was stirred at room temperature for 1.5 hours and then evaporated from carbon tetrachloride (3×15 mL). To the residue dissolved in DMF (2.0 mL) at 0° C. was added a solution of 16, prepared in Example III, (450 mg, 1.16 mmol) in DMF (2.0 mL). The reaction was stirred for 18 hours, and concentrated. The residue was partitioned between EtOAc and pH 4.0 buffer. The aqueous phase was extracted with EtOAc (2×25 mL). The combined EtoAc extracts were washed with brine, dried and evaporated to give an oil. Chromatography (99:1 EtOAc/HOAc) provided 29 as a white foam (0.39 g, 0.53 mmol) in 46% yield.

Conversion of 29 to TFP ester 30

To an ice cold solution of 29 (390 mg, 0.53 mmol) in acetonitrile (1.0 mL) were added tetrafluorophenol (115 mg, 0.69 mmol) and DCC (131 mg, 0.63 mmol). The reaction was stirred for 18 hours, cooled to 0° C., filtered, and the filtrate was evaporated. Chromatography (75% EtOAc/Hexanes 1% HOAc) gave 30 as an oil (400 mg, 0.45 mmol) in 85% yield.

Cleavage of T-butyl and Trichloroethylester Protecting Groups to Give 32

A solution of 30 (200 mg, 0.22 mmol) in formic acid (7.5 mL) was stirred for 3 hours and then evaporated. The residue was chromatographed (99:1, EtOAc/HOAc) to give 31 as a white foam. To a solution of 31 (180 mg, 0.22 mmol) in THF (1.44 mL) were added Zn (144 mg, 2.20 mmol) and 1.0M $KH_2PO_4$ (0.29 mL). The reaction was stirred 40 minutes. Additional Zn (150 mg, 2.29 mmol) and 1.0M $KH_2PO_4$ (0.29 mL, were added. The reaction was stirred for 30 minutes. Additional Zn (150 mg, 2.29 mmol) and 1.0M $KH_2PO_4$ (0.29 mL) were added. The reaction was stirred 20 minutes, filtered, rinsed with acetonitrile (25 mL), 50% aqueous acetonitrile (10 mL), and evaporated to give a solid (140 mg). One third of the crude product was purified by preparative LC on a semi-analytical C-18 reverse LC column with 45% acetonitrile/water 1% acetic acid as the mobile phase. The final chelating compound 32 was obtained as a white film (17 mg, 0.025 mmol). Thus projected yield if all of the crude product had been LC prepped is 34% for the two deprotection steps. Compound 32 is a chelating compound of the present invention.

EXAMPLE VII

Synthesis of DAP-disuccinate 36

Figure 7:
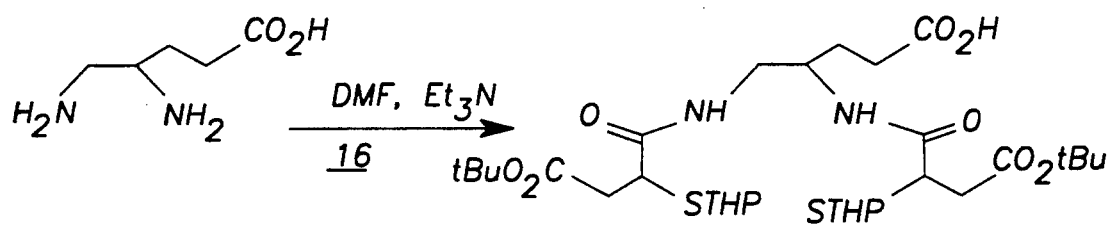
Figure 7:
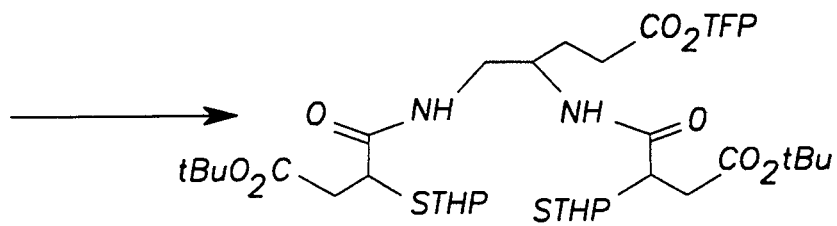
Figure 7:
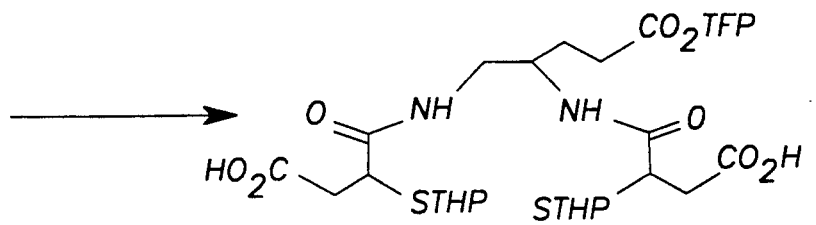

The synthesis procedure is outlined in FIG. 7.

Condensation of 4,5-Diaminopentanoic Acid (DAP) with Succinate Reagent 16

To an ice cold suspension of DAP (338 mg, 1.65 mmol) and 16, prepared in Example III, (1160 mg, 3.0 mmol) in DMF (3.5 mL) was added triethylamine (1.03 mL, 5.77 mmol). The ice bath was allowed to melt and the reaction was stirred at room temperature for 18 hours. The solution was concentrated. The residue was partitioned between EtOAc and pH 4.0 buffer. The aqueous phase was washed with EtOAc (2×50 mL). The combined EtOAc extracts were washed with brine, dried, and evaporated. The residue was chromatographed (50% EtOAc/Hexanes 1% HOAc, 400 mL, then 65% EtOAc/Hexanes 1% HOAc) to give 34 as a white solid (770 mg, 1.13 mmol) in 69% yield.

Conversion of 34 to TFP ester 35

To an ice cold solution of 34 (363 mg, 0.50 mmol) in acetonitrile (1.0 mL) and methylene chloride (0.1 mL) were added tetrafluorophenol (113 mg, 0.68 mmol) and DCC (129 mg, 0.62 mmol). The ice bath was allowed to melt and the reaction was stirred at room temperature for 18 hours. The reaction was cooled to 0° C., treated with 2 drops acetic acid, and filtered. The filtrated was evaporated. The residue was chromatographed (30% EtOAc/Hexanes) to give 35 as a white foam (350 mg, 0.41 mmol) in 80% yield.

Conversion of 35 to discuccinate ligand 36

A solution of 35 (230 mg, 0.27 mmol) was stirred for 2 hours. The solution was coevaporated with toluene and dried in vacuo. Crude 36 was obtained as a white solid (200 mg). Half of the product was purified by preparative LC on a C-18 semi-prep reverse phase column. The first eluting major peak, referred to as "A", was obtained in 22% yield as a white solid (19 mg, 0.03 mmol). The second eluting major peak, referred to as "B" was obtained in 39% yield (30 mg, 0.05 mmol). High resolution FAB-MS showed parent ions and similar fragmentation patterns for both isomers "A" and "B". Compound 36 (both isomers thereof) is a chelating compound of the present invention.

EXAMPLE VIII

Preparation of Radionuclide Metal Chelates and Attachment of the Chelates to Targeting Proteins 1. $^{99m}$Tc Chelates: Each of the four chelating compounds synthesized in Examples I–VII (Compounds 21, 28, 32, and 36) was radiolabeled with $^{99m}$Tc according to the following procedure:

One mL of sterile water for injection was added to a sterile vial containing a stannous gluconate complex (50 mg sodium gluconate and 1.2 mg stannous chloride dihydrate, available from Merck Frosst, Canada, in dry solid form) and the vial was gently agitated until the contents were dissolved. A sterile insulin syringe was used to inject 0.1 mL of the resulting stannous gluconate solution into an empty sterile vial. Sodium pertechnetate (0.75 mL, 75–100 mCi, eluted from a $^{99}$Mo/$^{99}$Tc generator purchased from DuPont, Mediphysics, Mallinckrodt or E. R. Squibb) was added, and the vial was agitated gently to mix the contents, then incubated at room temperature for 10 minutes to form a $^{99m}$Tc-gluconate complex.

In an alternative procedure for providing the $^{99m}$Tc-gluconate exchange complex, the kit includes a vial containing a lyophilized preparation comprising 5 mg sodium gluconate, 0.12 mg stannous chloride dihydrate, about 0.1 mg gentisic acid as a stabilizer compound, and about 20 mg lactose as a filler compound. The amount of gentisic acid may vary, with the stabilizing effect generally increasing up to about 0.1 mg. Interference with the desired reactions may occur when about 0.2 mg or more gentisic acid is added. The amount of lactose also may vary, with amounts between 20 and 100 mg, for example, being effective in aiding lyophilization. Addition of stabilizer and a filler compound is especially important when the vial contained these relatively small amounts of sodium gluconate and stannous chloride (compared to the alternative embodiment above). One mL of sodium pertechnetate (about 100 mCi) was added directly to the lyophilized preparation. The vial was agitated gently to mix the contents, then incubated as described above to form the $^{99m}$Tc-gluconate complex.

A separate vial containing 0.3 mg of a chelating agent in dry solid form was prepared by dispensing a solution of 0.3 mg chelating agent in acetonitrile into the vial, then removing the solvent under N$_2$ gas. To this vial was then added 0.87 mL of 100% isopropyl alcohol, and the vial was gently shaken for about 2 minutes to completely dissolve the chelating compound. Next, 0.58 mL of this solution of the chelating agent was transferred to a vial containing 0.16 mL of glacial acetic acid/0.2N HCl (2:14), and the vial was gently agitated. Of this acidified solution, 0.5 mL was transferred to the vial containing the $^{99m}$Tc-gluconate complex, prepared above. After gentle agitation to mix, the vial was incubated in a 75° C.±2° C. water bath for 15 minutes, then immediately transferred to a 0° C. ice bath for 2 minutes.

To a separate vial containing 10 mg of the Fab fragment of a monoclonal antibody in 0.5 mL of phosphate-buffered saline, was added 0.37 mL of 1.0M sodium bicarbonate buffer, pH 10.0. The Fab fragment was generated by treating the monoclonal antibody with papain according to conventional techniques. The monoclonal antibody, designated NR-LU-10, recognizes a pancarcinoma antigen. The vial was gently agitated. Other targeting proteins may be substituted for the NR-LU-10 Fab fragment.

The vial containing the acidified solution of the $^{99m}$Tc-labeled chelate (see above) was removed from the ice bath, 0.1 mL of the sodium bicarbonate buffer was added, and the vial was agitated to mix. Immediately, the buffered antibody solution (above) was added, gently agitated to mix and incubated at room temperature for 20 minutes to allow conjugation of the radiolabeled chelate to the antibody.

A column containing an anion exchanger, either DEAE-Sephadex or QAE-Sephadex, was used to purify the conjugate. The column was prepared under aseptic conditions as follows. Five 1 mL QAE- Sephadex columns were connected end-to-end to form a single column. Alternatively, a single 5 mL QAE-Sephadex column may be used. The column was washed with 5 mL of 37 mM sodium phosphate buffer, pH 6.8. A 1.2μ filter (available from Millipore) was attached to the column, and a 0.2μ filter was attached to the 1.2μ filter. A 22-gauge sterile, nonpyrogenic needle was attached to the 0.2μ filter.

The reaction mixture was drawn up into a 3 mL or 5 mL syringe, and any air bubbles were removed from the solution. After removal of the needle, the syringe was connected to the QAE-Sephadex column on the end opposite the filters. The needle cap was removed from the 22-gauge needle attached to the filter end of the column and the needle tip was inserted into a sterile, nonpyrogenic test tube. Slowly, over 2 minutes, the reaction mixture was injected into the column. The eluant collected in the test tube was discarded. The now empty syringe on top of the column was replaced with a 5 mL syringe containing 5 mL of 75 mM (0.45% sodium chloride solution (from which air bubbles had been removed). The needle at the other end of the column was inserted aseptically into a sterile, nonpyrogenic 10 mL serum vial. Slowly, over 2 minutes, the NaCl solution was injected into the column, and the eluent was collected in the serum vial.

The resulting radiolabeled antibody fragments may be represented as follows:

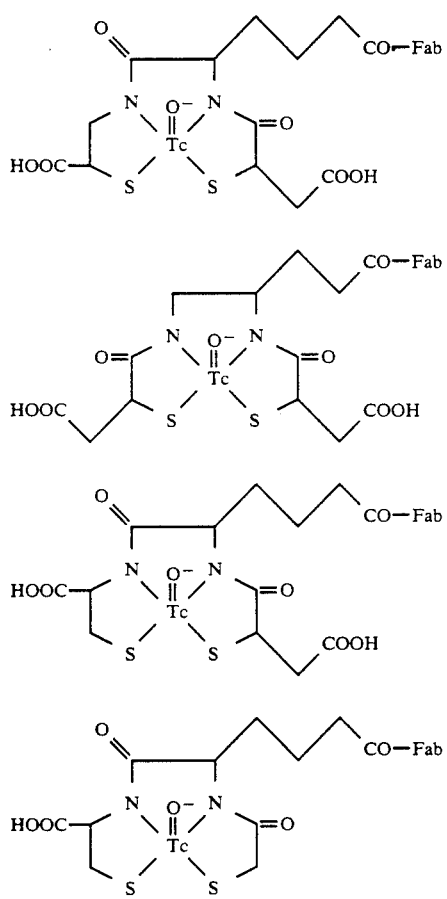

2. $^{188}$Re Chelates

The same chelating compounds may be radiolabeled with $^{188}$Re by a procedure similar to the $^{99m}$Tc labeling procedure. Sodium perrhenate produced from a W-188/Re-188 research scale generator is combined with citric acid (a preferred complexing agent for $^{188}$Re), a reducing agent, and preferably gentisic acid and lactose. The resulting $^{188}$Re-citrate exchange complex is heated with the desired chelating compound, as above. A $C_{18}$ reversed phase low pressure material (Baker $C_{18}$ cartridges) may be used to purify the $^{188}$Re-chelate. A monoclonal antibody or fragment thereof is reacted with the chelate in a buffered solution to bind the chelate thereto, as described for the $^{99m}$Tc procedure. A Sephadex G-25 column may be used to purify the radiolabeled antibody.

EXAMPLE IX

Biodistribution of the four $^{99m}$Tc-labeled antibody fragments prepared in Example VIII was analyzed in a rat model. 100 μg of protein (about 0.5 mCi) was administered intravenously into Sprague-Dawley rats. Each of the four types of radiolabeled antibody fragments (i.e., NR-LU-10 Fab fragments radiolabeled with one of the four different chelating compounds) was injected into three rats. Biodistribution was analyzed at 6 hours post-injection by isolating intestines and kidneys and determining the mCi of injected radioactivity per gram of these tissues, using a dose calibrator. The percentage of injected dose per gram of intestinal and kidney tissue was calculated and averaged to give the mean value for each group of three animals.

The results were compared with data on intestinal localization of radioactivity for radiolabeled antibody fragments of the following formula I (wherein the fragments are labeled with an $N_2S_2$ chelate that lacks carboxylic acid substituents):

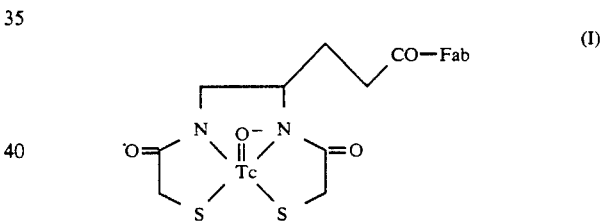

A reduction in intestinal localization of radioactivity was demonstrated for each of the four radiolabeled antibody fragments of the present invention, compared to the radiolabeled fragment of formula (I).

EXAMPLE X

Preparation of Radiolabeled Antibody Fragments

1. $^{99m}$Tc Chelates: Chelating compounds 21 and 36 (synthesized in Examples IV and VII, respectively) were radiolabeled with $^{99m}$Tc according to the following procedure (a preferred procedure for these two chelating compounds):

One mL of sterile water for injection was added to a sterile vial containing a stannous gluconate complex (50 mg sodium gluconate and 1.2 mg stannous chloride dihydrate, available from Merck Frosst, Canada, in dry solid form) and the vial was gently agitated until the contents were dissolved. A sterile insulin syringe was used to inject 0.1 mL of the resulting stannous gluconate solution into an empty sterile vial. Sodium pertechnetate (0.75 mL, 75-100 mCi, eluted from a $^{99}$Mo/$^{99}$Tc generator purchased from Dupont, Mediphysics, Mallinckrodt or E. R. Squibb) was added, and the vial was agitated gently to mix the contents, then incubated at room temperature for 10 minutes to form a $^{99m}$Tc-gluconate complex.

A separate vial containing 0.3 mg of the chelating agent (21 or 36) in dry solid form was prepared by dispensing a solution of 0.3 mg chelating agent in acetonitrile into the vial, then removing the solvent under $N_2$ gas. To this vial was then added 0.87 mL of 100% isopropyl alcohol, and the vial was gently shaken for about 2 minutes to completely dissolve the chelating compound. Next, 0.58 mL of this solution of the chelating agent was transferred to a vial containing 0.16 mL of glacial acetic acid/0.2N HCl (2:14), and the vial was gently agitated. Of this acidified solution, 0.5 mL was transferred to the vial containing the $^{99m}$Tc-gluconate complex, prepared above. After gentle agitation to mix, the vial was incubated in a 75° C. ±2° C. water bath for 15 minutes, then immediately transferred to a 0° C. ice bath for 2 minutes.

For compound 36, and whenever the radiolabeling yield for compound 21 was below 40%, the radiolabeled chelate was purified prior to conjugation to an antibody as follows. An SPE-$C_{10}$ extraction column (a reversed phase column available from Baker) was conditioned by washing with 2 mL of ethanol followed by 2 mL of sterile water. The reaction mixture was then loaded onto the top of the column. The column was washed with 2 mL aliquots of 1% ethanol/0.01M phosphate (pH=7.0) 6-8 times and dried for 10 minutes under vaccuum. The $^{99m}$Tc chelates were then eluted using 0.5 mL of $CH_3CN$ for compound 21 and 1 mL of $CH_3CN$ for compound 36. The $CH_3CN$ was evaporated under a stream of $N_2$ prior to the conjugation with antibody.

The $^{99m}$Tc chelates thus purified were attached to the Fab fragment of a monoclonal antibody (designated NR-LU-10) as described in Example VIII. Other targeting proteins may be substituted for the NR-LU-10 antibody fragment.

EXAMPLE XI

Preparation of $^{99m}$Tc Chelate Using Chelating Compound 32

Compound 32 (prepared in Example VI) was radiolabeled by the following procedure, which is preferred for this particular chelating compound:

One mL of $NaTcO_4$ (~100 mCi) was added to a lyophilized preparation containing 5.0 mg of sodium gluconate, 0.12 mg of stannous chloride dihydrate, 0.1 mg of gentisic acid, and 20 mg of lactose (lyophilization pH=3.5). After incubating the vial at room temperature for 2 minutes, 0.1 mL of compound 32 (1 mg/mL in 90% isopropyl alcohol) was added. Then 0.300 mL of isopropyl alcohol and 0.060 mL of 0.1N HCl were added. 2 cc of air was added into the vial and incubated at 75° C. for 15 minutes. The vial was then immediately transferred to a 0° C. ice bath for 2 minutes.

The resulting $^{99m}$Tc chelate was attached to an antibody fragment as described in Example VIII. Other targeting proteins may be substituted for the antibody fragment.

What is claimed is:

1. A compound of the formula:

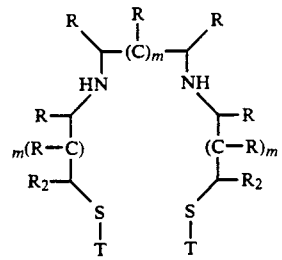

wherein:
each R independently represents =O, $H_2$, lower alkyl, $-(CH_2)_n-COOH$, or $R_1-Z$;
n is 0 to 3;
$R_1$ represents a lower alkyl or substituted lower alkyl group;
Z represents a protein conjugation group or a antibody or antigen binding fragment of said antibody;
each $R_2$ independently represents $H_2$, lower alkyl, $-(CH_2)_n-COOH$, or $R_1-Z$;
each m is 0 or 1, with at most one m=1;
each T represents a sulfur protecting group; and
the compound comprises at least one $-(CH_2)_n-COOH$ substituent and one $-R_1-Z$ substituent.

2. The compound of claim 1 wherein $R_1$ is a methylene chain comprising from two to three carbon atoms.

3. The compound of claim 1 wherein two R substituents are =O.

4. The compound of claim 1 wherein at least one $R_2$ substituent is $-(CH_2)_n-COOH$.

5. The compound of claim 1 wherein at least one T represents a hemithioacetal sulfur protecting group.

6. The compound of claim 1 wherein the protein conjugation group is selected from the group consisting of active esters, isothiocyanates, amines, hydrazines, thiols, and maleimides, wherein when an amine is the protein conjugation group, a methylene group is immediately adjacent to the amine.

7. The compound of claim 6 wherein the protein conjugation group is an active ester.

8. The compound of claim 1 wherein the targeting protein is a monoclonal antibody or or an antigen binding fragment thereof.

9. A compound of the following formula:

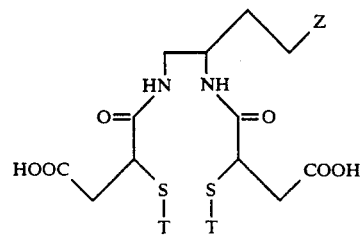

wherein each T represents a hemithioacetal sulfur protecting group and Z represents an active ester.

10. A compound of the following formula:

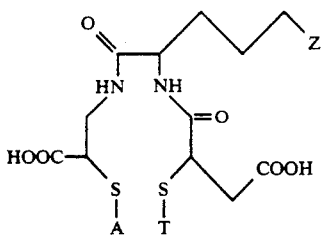

wherein A represents an acetamidomethyl sulfur protecting group, T represents a hemithioacetal sulfur protecting group, and Z represents an active ester.

11. A compound of the following formula:

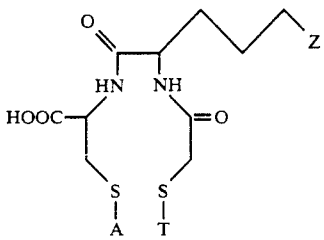

wherein A represents an acetamidomethyl sulfur protecting group, T represents a hemithioacetal sulfur protecting group, and Z represents an active ester.

12. A compound of the following formula;

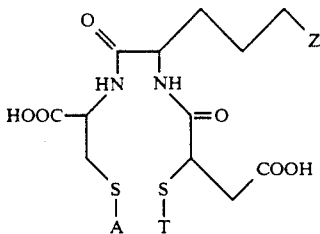

wherein A represents an acetamidomethyl sulfur protecting group, T represents a hemithioacetal sulfur protecting group, and Z represents an active ester.

13. A radiolabeled antibody of the formula:

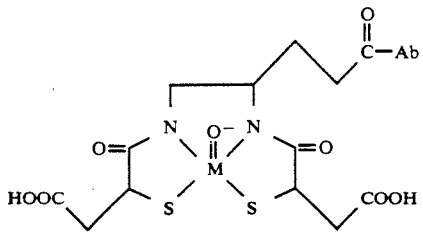

wherein M represents a radionuclide metal selected from the group consisting of $^{99m}$Tc, $^{186}$Re, and $^{188}$Re; and Ab represents an antibody or antigen binding fragment of said antibody.

14. A radiolabeled antibody of the formula:

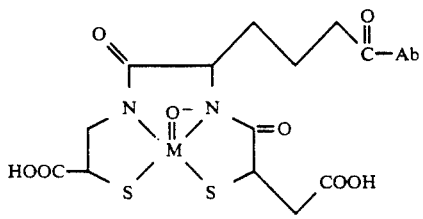

wherein M represents a radionuclide metal selected from the group consisting of $^{99m}$Tc, $^{186}$Re, and $^{188}$Re; and Ab represents an antibody or antigen binding fragment of said antibody.

15. A radiolabeled antibody of the formula:

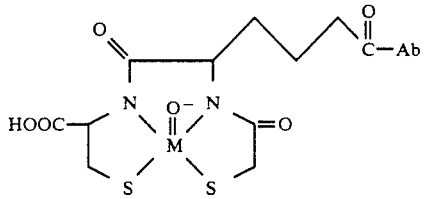

wherein M represents a radionuclide metal selected from the group consisting of $^{99m}$Tc, $^{186}$Re, and $^{188}$Re; and Ab represents an antibody or antigen binding fragment of said antibody.

16. A radiolabeled antibody of the formula:

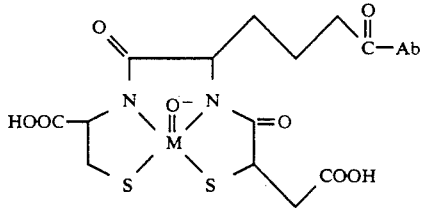

wherein M represents a radionuclide metal selected from the group consisting of $^{99m}$Tc, $^{186}$Re, and $^{188}$Re; and Ab represents an antibody or antigen binding fragment of said antibody.

* * * * *